(12) United States Patent
Sander et al.

(10) Patent No.: US 8,007,107 B2
(45) Date of Patent: Aug. 30, 2011

(54) ILLUMINATING APPARATUS FOR AN OPERATING MICROSCOPE

(75) Inventors: Ulrich Sander, Rebstein (CH); Manfred Kuster, Widnau (CH)

(73) Assignee: Leica Microsystems (Schweiz) AG, Heerbrugg (CH)

( * ) Notice: Subject to any disclaimer, the term of this patent is extended or adjusted under 35 U.S.C. 154(b) by 0 days.

(21) Appl. No.: 12/795,932

(22) Filed: Jun. 8, 2010

(65) Prior Publication Data

US 2010/0315593 A1    Dec. 16, 2010

(30) Foreign Application Priority Data

Jun. 10, 2009  (DE) .................. 10 2009 026 909
Aug. 4, 2009   (DE) .................. 10 2009 028 229

(51) Int. Cl.
*A61B 3/10*   (2006.01)
*A61B 3/02*   (2006.01)
*G02B 21/00*  (2006.01)
*G02B 21/06*  (2006.01)

(52) U.S. Cl. ......... 351/221; 351/243; 359/368; 359/389
(58) Field of Classification Search .......... 351/200–246; 359/368, 369, 385–390, 200–246
See application file for complete search history.

(56) References Cited

U.S. PATENT DOCUMENTS

| 4,871,245 A * | 10/1989 | Ishikawa et al. ............ 359/363 |
| 5,760,952 A * | 6/1998 | Koetke ......................... 359/389 |
| 6,011,647 A * | 1/2000 | Geschwentner ............. 359/389 |
| 2003/0161037 A1 | 8/2003 | Sander |
| 2004/0174591 A1 | 9/2004 | Sander |

FOREIGN PATENT DOCUMENTS

| DE | 33 27 672 A1 | 2/1985 |
| DE | 10 2007 008 635 A1 | 9/2007 |
| JP | 11038327 A | 2/1999 |
| JP | 11109254 A | 4/1999 |

* cited by examiner

*Primary Examiner* — Mohammed Hasan
(74) *Attorney, Agent, or Firm* — Hodgson Russ LLP

(57) ABSTRACT

The present invention relates to an illuminating apparatus for an operating microscope comprising two observation beam paths (152, 154) for a first observer (main surgeon) and two observation beam paths (156, 158) for a second observer (assisting surgeon), comprising an illuminating system (102; 106a, 108a, 172) and deflecting means (118, 120, 170), for deflecting light emanating from the illumination system onto an object (200) that is to be observed, wherein the deflecting device comprises a first deflecting element (118) which is associated with a first observation beam path (152) of the first observer and a first observation beam path (156) of the second observer, and a second deflecting element (120) which is associated with a second observation beam path (154) of the first observer and a second observation beam path (158) of the second observer.

22 Claims, 4 Drawing Sheets

ILLUMINATING APPARATUS FOR AN OPERATING MICROSCOPE

CROSS REFERENCE TO RELATED APPLICATIONS

Figure 1:
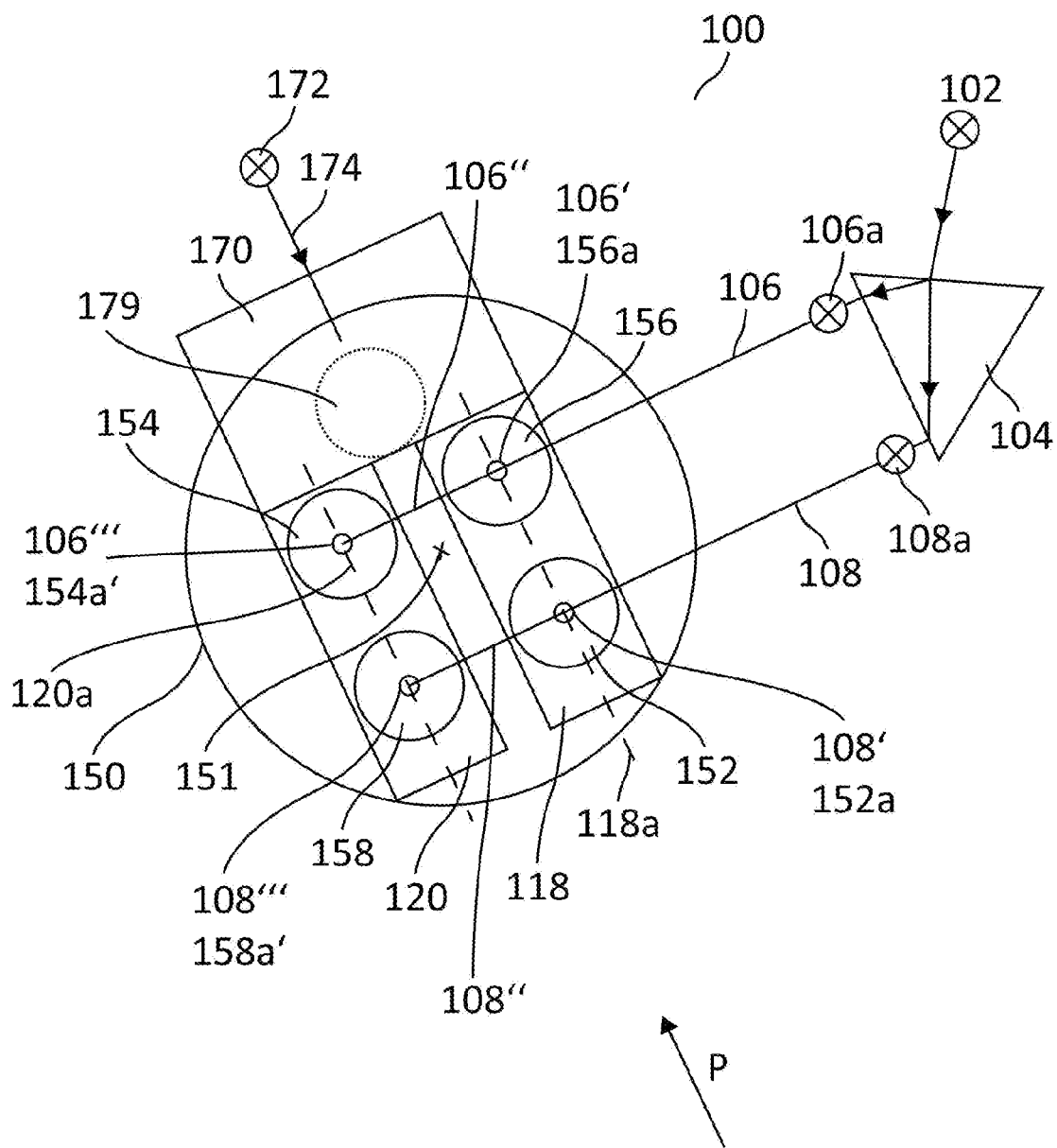

This application claims priority of the German patent application 10 2009 026 909.6 filed Jun. 10, 2009, the entire disclosure of which is incorporated by reference herein. This application also claims priority of German patent application 10 2009 028 229.7 filed Aug. 4, 2009, the entire disclosure of which is incorporated by reference herein.

FIELD OF THE INVENTION

The present invention relates to an illuminating apparatus for a microscope, particularly for a stereomicroscope for performing surgical operations, to illuminate an object to be viewed.

BACKGROUND OF THE INVENTION

Illuminating apparatus for operating microscopes generally use an illumination beam path (or illumination beam) which is at an angle in the region of about 6° to the observation beam path (or observation beam) (so-called 6° illumination). This avoids unwanted shadow formation which would occur in the presence of larger angles between the observation beam path and the illumination beam path.

Eye surgery places even more special demands on the illumination of a microscope. First of all, the image has sufficient plasticity at an illumination angle of about 6°. However, for certain ophthalmic observations or interventions it is necessary to produce the so-called red reflex. In this, the light reflected back by the retina causes the pupil of the eye being operated on to shine with a reddish light. This method of illumination is of major importance in cataract operations, for example, as any residual tissue can be identified particularly easily in the back light of the red reflex. The production of the red reflex requires smaller angles between the observation beam path and the illumination beam path, the preferred angles being in the range from 0° to 2° (so-called 0° or 2° illumination).

Operating microscopes which are constructed with two pairs of stereoscopic observation beam paths for a first observer (main surgeon) and a second observer (assisting surgeon) often have a deficiency in that the red reflex shows up very well for the main surgeon but only to an inadequate degree for the co-observer. The latter receives a good red reflex in only one of his two observation channels, either to the right or to the left of the main surgeon, depending on his position. This interferes with the stereoscopic observation.

DE 04028605 discloses an illuminating apparatus for a surgical microscope with an illuminating system which is arranged outside the optical axis of the microscope objective lens, and the operating field is illuminated through the microscope objective lens parallel to the axis of the objective lens, and a deflecting element on the side of the microscope objective lens remote from the object, which illuminates the operating field with a fraction of the illuminating light along the axis of the objective lens. This illuminating apparatus is characterised in that the illuminating system is equipped on the objective lens side with a reflecting element which reflects the illuminating light towards the microscope objective lens parallel to the axis of the objective lens, and the deflecting element illuminates the operating field at an angle of inclination to the axis of the objective lens which is less than the angle of inclination at which the reflecting element illuminates the operating field. The larger angle of inclination is preferably 6° here, while the smaller angle may vary from 0° to 6°. The illuminating apparatus described in this publication does not contain any solution, for example, to the problem of supplying a red reflex for a second observer (assisting surgeon).

DE 103 11 000 B4 discloses an illuminating apparatus for a microscope, particularly an operating microscope, having at least one observation beam path, with an illuminating system and a deflecting device for deflecting light emanating from a light source onto an object that is to be observed, e.g. an eye that is to be operated on, wherein the deflecting device allows the object to be illuminated at different illuminating angles with respect to the at least one observation beam, and wherein the deflecting device comprises two deflecting elements that are at least partially constructed as physical beam splitters. In order to provide a 6° and 2° illumination for a main surgeon and an assisting surgeon, this illuminating apparatus uses three deflecting elements.

SUMMARY OF THE INVENTION

The present invention seeks to provide an illuminating apparatus for an operating microscope which is as simple as possible, compact in construction and cheap to produce and which can be used simultaneously by a first observer (main surgeon) and a second observer (assisting surgeon). This object is achieved by an illuminating apparatus having the features described herein. Accordingly, the invention also provides a stereomicroscope, particularly an operating microscope, of compact design.

The present invention distances itself from the idea, found throughout the prior art, that the observation beams of the main surgeon and the observation beams of the assisting surgeon are each provided exclusively by deflecting elements associated only with the observation beams of the main surgeon and only with the observation beams of the assisting surgeon, by means of which an illuminating beam path emanating from a light source is deflected onto an object that is to be observed.

It is provided, according to the invention, that a first deflecting element is associated with a first observation beam path or observation channel of the main surgeon and a first observation beam path of the assisting surgeon, in other words is assigned to or illuminates these two observation beam paths. The second observation beam paths for the main surgeon and assisting surgeon in each case are associated with a second deflecting element. The idea according to the invention can also be described as follows: a first illumination beam path is assigned to or supplies a first observation beam path of the main surgeon and a first observation beam path of the assisting surgeon, while at the same time a second illumination beam path is assigned to a second observation beam path of the main surgeon and a second observation beam path of the assisting surgeon. In all, as will be obvious without further explanation, the two observation beam paths of the main surgeon provide a stereoscopic view for the main surgeon, and the two observation beam paths of the assisting surgeon provide a stereoscopic view for the assisting surgeon.

The orientation of the illumination beam paths with respect to the deflecting elements can also be described in terms of the stereo base of the main surgeon or of the assisting surgeon. The (parallel) observation beam paths of the main surgeon define the stereo base of the main surgeon by their spacing from one another. Analogously, the (parallel) observation beam paths of the assisting surgeon define the stereo base of the assisting surgeon. As previously mentioned, the deflecting elements each serve to illuminate one observation beam path of the main surgeon and one observation beam path of the assisting surgeon. A line passing through these two observation beam paths represents the longitudinal axis of the deflecting element in question. The present invention is characterised in that the stereo bases of the main surgeon or assisting surgeon extend at an inclined angle to these longitudinal axes of the deflecting elements, particularly at an angle of 30-60°, preferably at 45°.

As a result of this departure from conventional illumination arrangements it is possible according to the present invention to operate two observation beam paths of a main surgeon and two observation beam paths of an assisting surgeon using only two deflecting elements. This results, in particular, in an optimum red reflex for both the main surgeon and the assisting surgeon. Moreover, an illuminating apparatus that requires only two deflecting elements for the purpose stated is very compact in construction. Furthermore, it is found to be advantageous that the illumination beam paths striking the deflecting elements can be irradiated at an angle to the imaginary lines joining the two observation beam paths of the main surgeon and of the assisting surgeon respectively.

Especially, according to the invention, the illumination system is adapted for providing two parallel illumination beams, wherein the deflecting device deflects the parallel illumination beams onto the object that is to be observed. First and second deflecting elements are semitransparent (partly transparent), wherein the horizontal projection of the first deflecting element essentially overlaps the first observation beam path of the first observer and the first observation beam path of the second observer, and the horizontal projection of the second deflecting element essentially overlaps the second observation beam path of the first observer and the second observation beam path of the second observer.

Advantageous embodiments of the invention are recited in the present specification.

According to a preferred embodiment of the illuminating apparatus according to the invention, the illuminating system used by means of which light is applied to the deflecting elements comprises a single light source. Such a light source may cooperate with a beam splitter element, for example a Köster's prism, so as to produce two suitable illumination beam paths. Alternatively, fibre bundles emanating from the light source may also be used to provide the illumination beam paths in question.

It is preferable if the two deflecting elements used according to the invention are used to provide 0° to 2° illumination for the first and second observer.

Expediently, the illuminating apparatus according to the invention comprises at least one other deflecting element for providing further illumination at a larger angle, particularly ambient illumination or 6° illumination. Due to the compact nature of the 0° or 2° illumination which requires only two deflecting elements according to the invention, other deflecting elements for the 6° illumination can be provided in a particularly simple and flexible manner.

The first deflecting element and the second deflecting element are expediently provided at the same distance from a main objective lens onto which they deflect the light obtained from the illumination system. Such an embodiment is very compact, particularly in the vertical or perpendicular direction.

According to a preferred embodiment it is also possible to arrange the third deflecting element at the same height as the first and second deflecting elements. By this measure it is also possible to produce a very compact illumination system which provides a 0° or 2° illumination and a 6° illumination.

Advantageously, the first and second deflecting elements are provided as partly transparent or semitransparent mirrors, i.e. physical beam splitters. Be it noted that the terms "partly transparent" and "semitransparent" are used synonymously throughout this specification. Especially, "semitransparent" shall include any kind of transparency, in which some percentage of light is transmitted and another percentage is reflected. Elements of this kind can be produced cheaply and compactly and are lightweight in construction. It is also possible for example to use prisms as deflecting elements. Semitransparent deflecting elements of this kind allow great freedom in positioning, including in particular in illumination beam paths.

The additional deflecting element may also be constructed as a semitransparent mirror element and/or as a mirror element that is fully reflective at least in parts. When a semitransparent mirror element is used it is possible in particular to illuminate an additional beam path, for example for documentation, while producing a red reflex. The use of a fully reflective mirror element allows particularly effective illumination.

According to another preferred embodiment of the illuminating apparatus according to the invention, the first and/or the second deflecting element is constructed to be fully reflective at least in parts. By this measure it is possible for example to construct areas of the deflecting elements located outside the observation beam paths to be fully reflective without affecting the observation beam paths. It is also possible, for example, to make small areas of the deflecting elements which are struck by the observation beam paths fully reflective. This measure can positively influence the red reflex, for example, without the observer noticing the fully reflective areas within the observation beam paths.

The illuminating apparatus according to the invention expediently has a device for reducing unwanted light reflexes and/or reflections within the operating microscope. A device of this kind may effectively prevent, in particular, crosstalk between individual channels of the operating microscope.

In connection with this it is preferable for the first and second deflecting elements to have polarising properties and for a λ/4 device (quarter wave plate or film) to be provided in the observation beam paths of the first and second observers, particularly between the object and the main objective lens, or between the main objective lens and the first and second deflecting elements. By means of to the polarising properties of the deflecting elements it is possible to ensure, for example, that linearly polarised light is transmitted or reflected only in one direction. Using the λ/4 device through which the beam paths pass twice on their way to and from the object, it is possible to rotate the plane of oscillation of the polarised light through 90°.

It is also preferable in this context for a λ/2 device (half wave plate or film) to be provided between the first and second deflecting elements. By means of a λ/2 device of this kind, reflections and reflexes caused by the main objective lens, for example, are further minimized.

According to another preferred embodiment the first and the second deflecting element are formed in a uniform glass block. Mounting in a glass block in this way also serves to reduce unwanted reflexes or reflections, as glass/air surfaces which may cause unwanted reflexes of this kind are minimised.

Further advantages will become apparent from the description of the attached drawings.

It will be understood that the features mentioned hereinbefore and those to be explained hereinafter may be used not only in the particular combination stated but also in other combinations or on their own, without departing from the scope of the present invention.

This invention will now be explained more fully by a description of preferred embodiments by way of example with reference to the attached Figures.

BRIEF DESCRIPTION OF THE DRAWING VIEWS

Figure 2:
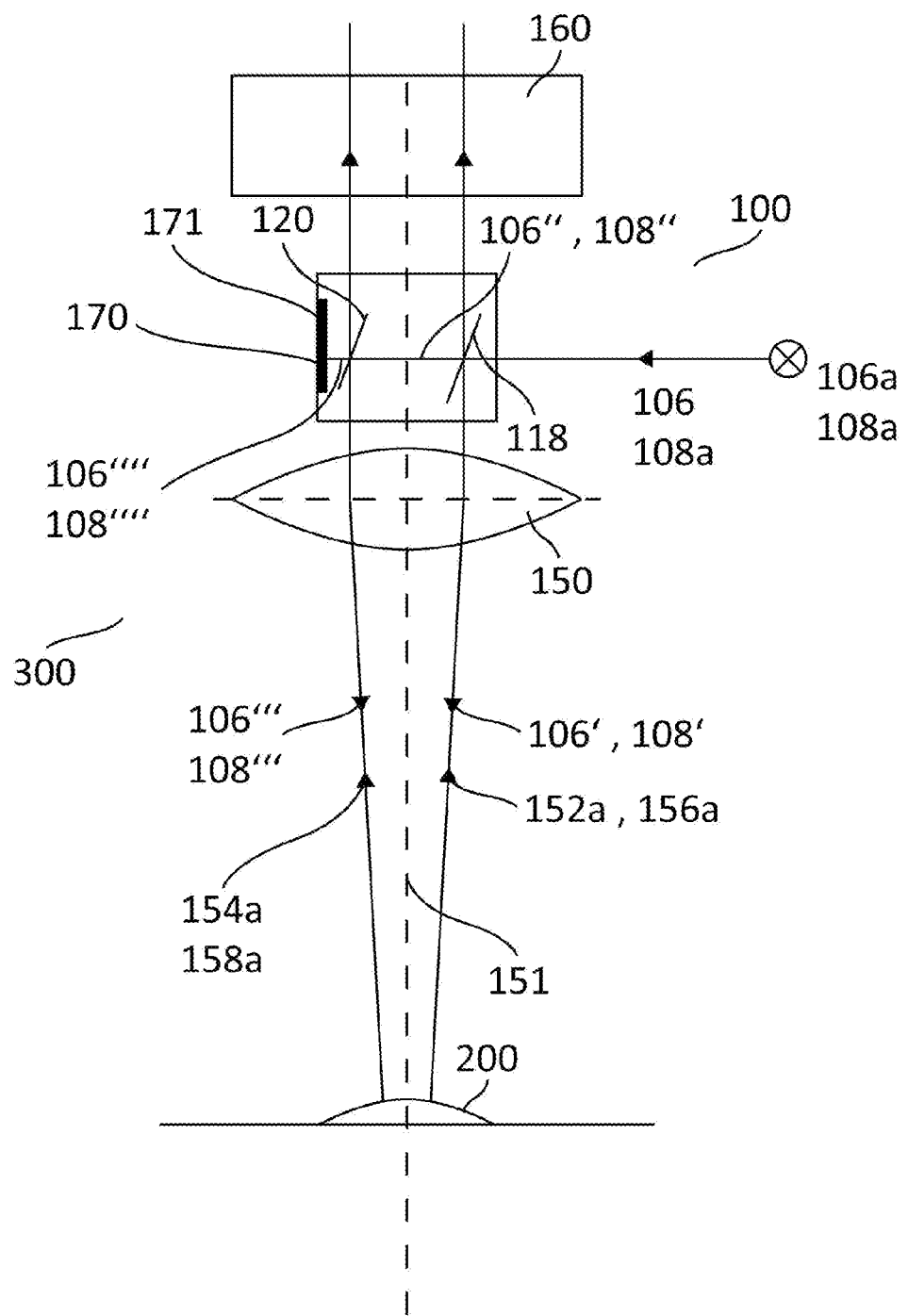
Figure 3:
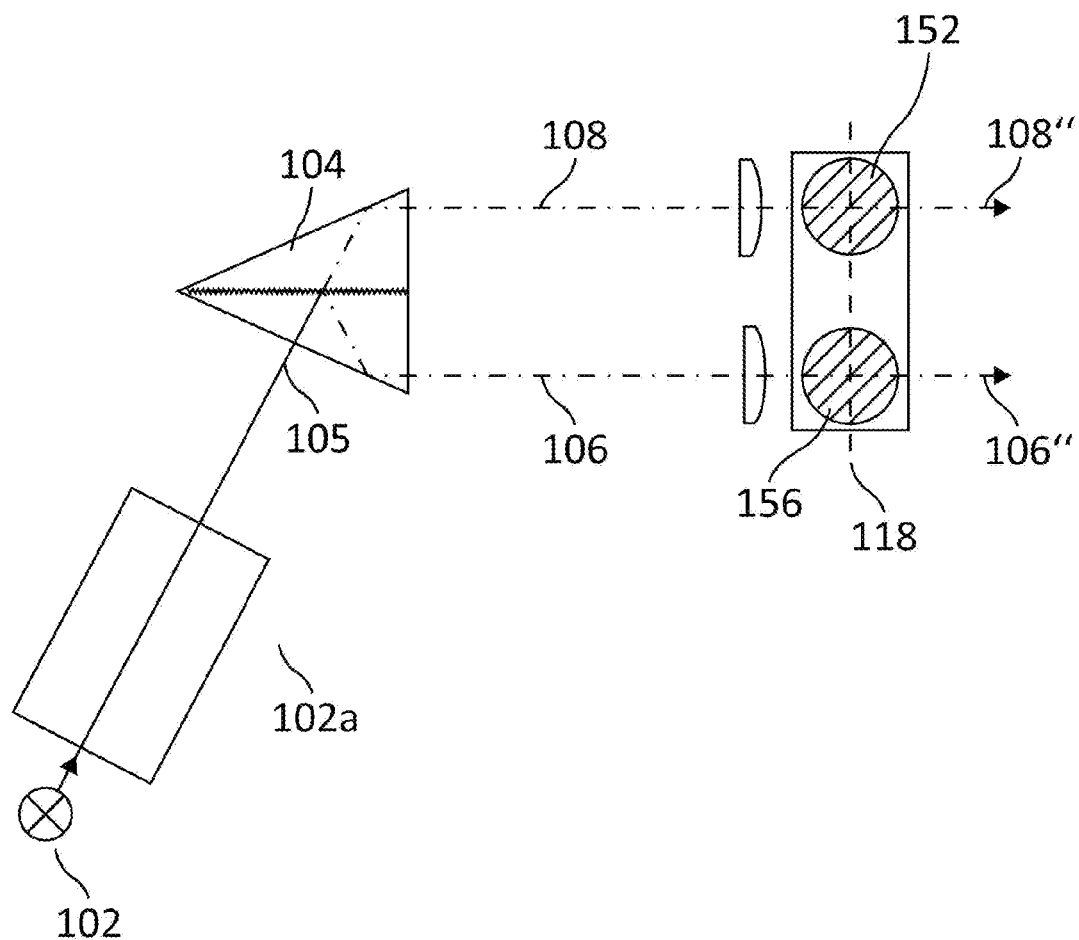
Figure 4:
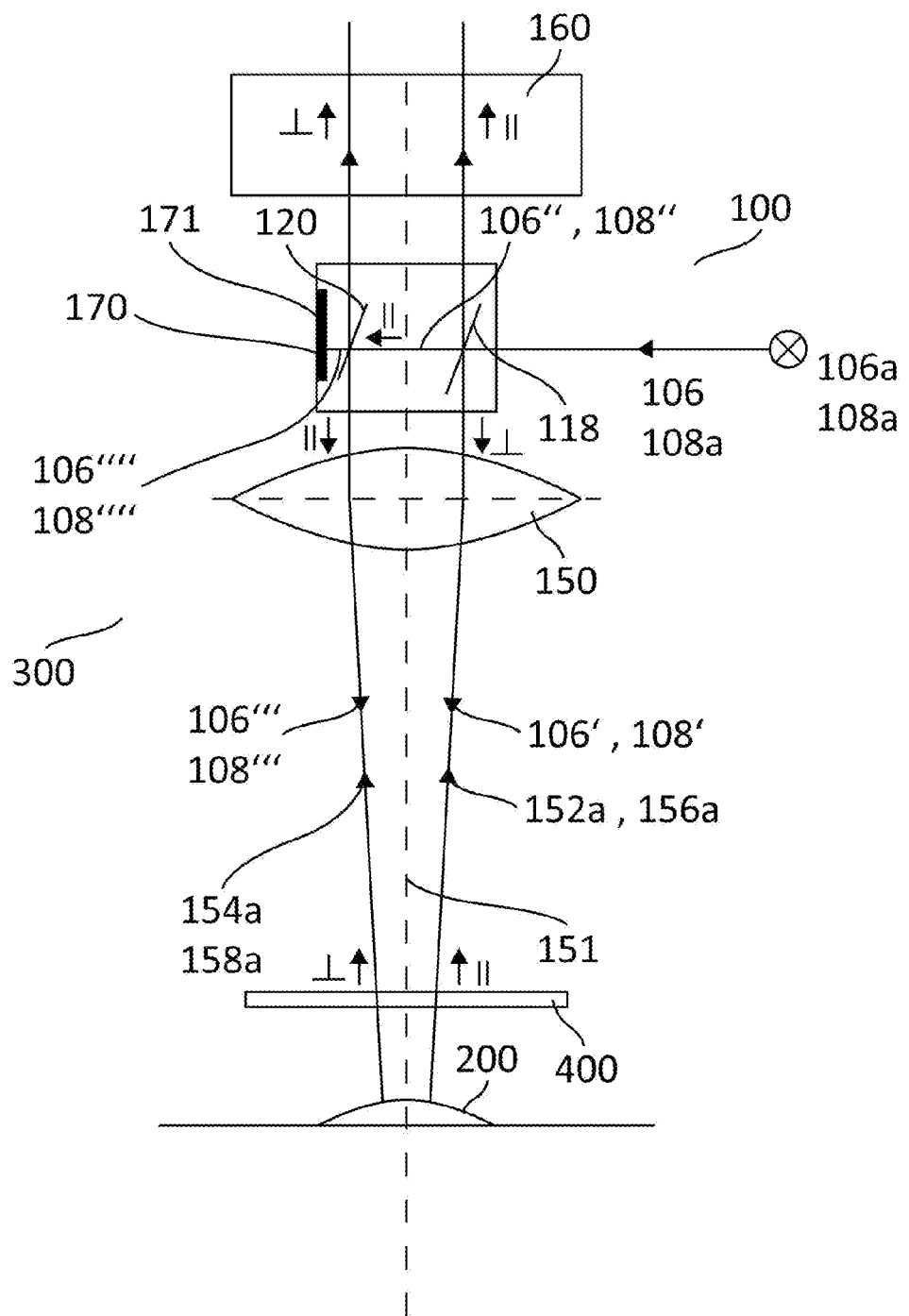

The drawings show:

FIG. 1: a plan view of a first preferred embodiment of an illuminating apparatus according to the invention, FIG. 2: a schematic side elevation of the illuminating apparatus in the direction of the arrow P in FIG. 1, FIG. 3: a plan view of a preferred detail of an illuminating apparatus according to the invention, and FIG. 4: a schematic side view, corresponding to FIG. 2, of another preferred embodiment of an illuminating apparatus according to the invention.

DETAILED DESCRIPTION OF THE INVENTION

In FIGS. 1 and 2 a preferred embodiment of the illuminating apparatus according to the invention cooperating with a main objective lens 150 and, downstream thereof, a magnification system (including the necessary tubes and eyepieces) 160 of a microscope 300 is generally designated 100.

The microscope 300 is a stereo operating microscope which provides two observation beam paths 152, 154 for a main surgeon and two further observation beam paths 156, 158 for an assisting surgeon. The observation channels are represented in FIG. 1 as circles and in FIG. 2 by means of the observation axis 152a, 154a, 156a, 158a associated therewith. There is no need to go into any further detail as to specific equipment (such as e.g. lens or zoom systems) for producing four observation channels of this kind within the scope of the present invention, which relates to an illuminating apparatus.

The illuminating apparatus 100 according to the invention comprises a light source 102. By means of a beam splitter 104 (schematically shown in FIG. 1) which may be constructed for example as a Köster's prism, (cf. FIG. 3), two illumination beam paths 106, 108 are generated. As will be apparent without any further explanation, these illumination beam paths 106, 108 may be regarded as light beams emanating from (virtual) light sources 106a, 108a. It is also possible to provide two (actual) light sources 106a, 108a instead of the light source 102 and beam splitter 104. It is also possible to use fibre illuminating apparatus. As can be seen, the illumination beam paths 106, 108 are preferably parallel.

The illuminating apparatus 100 also comprises two deflecting elements 118, 120 as the deflecting device.

The deflecting element 118, which the illumination beam paths 106, 108 strike first, is constructed as a semitransparent element (physical beam splitter), particularly a semitransparent mirror. The additional deflecting element 120 is also constructed as a semitransparent mirror. It is possible to construct areas of the deflecting element 118, 120 to be fully reflective, for example regions located outside or in the edge region of the observation beam paths. It is also possible to make small areas of the deflecting elements fully reflective in the middle of the observation beam paths, i.e. substantially in the region of the observation axes. This measure makes it possible to influence the red reflex, for example.

The deflecting elements 118, 120 or their longitudinal axes which can be defined as the connecting lines between the observation axes of their associated observation beam paths (longitudinal axis 118a of the deflecting element 118 and longitudinal axis 120a of the deflecting element 120 shown in dash-dot lines in FIG. 1) are oriented slantwise or at an angle of 45° relative to the stereo base of the main surgeon (imaginary connecting line between the observation axes 152a, 154a of the main surgeon) or the stereo base of the assisting surgeon (imaginary connecting line between the observation axes 156a, 158a of the assisting surgeon). The deflecting elements are arranged immediately adjacent to the optical axis 151 of the main objective lens 150, and thus provide a 0° or 2° illumination of the object 200.

As can be seen, the deflecting element 118 essentially overlaps the first observation beam path 152 of the first observer and the first observation beam path 156 of the second observer. The horizontal projection of the second deflecting element essentially overlaps the second observation beam path 154 of the first observer and the second observation beam path of the second observer. A complete overlap is also possible in both cases.

The illuminating apparatus also comprises a further deflecting element 170 which is acted upon by a further light source 172. The deflecting element 170 is arranged at a greater distance from the optical axis 151 of the main objective lens 150 and serves to provide a 6° illumination for the observation beam paths 152, 154, 156, 158, which is advantageous for increasing the contrast for users of the microscope. For operating techniques in which the red reflex is not needed, it may be sufficient to use only the 6° illumination. The deflecting element 170 is preferably constructed as a fully reflective mirror, and is also constructed at an angle of 45° with respect to the preferably horizontally extending further illumination beam path 174. It is possible to combine the light sources 102, 172 to form a single light source, and to provide the illumination beam paths 106, 108, 174 by means of suitable beam splitter devices and/or light conducting systems (fibre optics).

It is also possible to make the deflecting element 170 semitransparent, so that a further observation beam path 179 (shown by dash-dot lines) can be illuminated. A documentation device, for example, may be connected to this observation beam path 179. A 0° to 2° illumination, for example, may thus be provided for the observation beam path 179, thereby ensuring that the red reflex is also visible in connection with the documentation.

The essence of the invention lies in the special arrangement of the deflecting elements 118, 120 with respect to the observation beam paths 152, 154 of the main surgeon and 156, 158 of the assisting surgeon.

As can be seen in the Figures, the first deflecting element 118 is associated with the first observation beam path 152 of the main surgeon and the first observation beam path 156 of the assisting surgeon. This means that the horizontal projection of the deflecting element 118, as shown in FIG. 1, substantially overlaps with the first observation beam path 152 of the main surgeon and the first observation beam path 156 of the assisting surgeon. The illumination beam paths 106, 108 are partly deflected through 90° at the first deflecting element 118 in the direction of the main objective lens 150 (partial beam paths 106', 108') and partly transmitted without being deflected (partial beam paths 106", 108").

The partial beam paths 106", 108" that are not deflected at the first deflecting element 118 strike the second deflecting element 120 which is associated analogously with the second observation beam path 154 of the main surgeon and the second observation beam path 158 of the assisting surgeon. The partial beam paths 106", 108" are partly deflected through 90° in the direction of the main objective lens (partial beam paths 106''', 108'''). As the second deflecting element 120 is also semitransparent in construction, part of the partial beam paths 106'', 108'' is also transmitted (106'''', 108''''), and expediently strikes a light trap (171).

The illumination system shown provides both the main surgeon and the assisting surgeon with an optimum red reflex, and this is achieved with only two deflecting elements 118, 120 and preferably with only one light source 102.

According to the embodiment as shown in FIGS. 1 and 2, the two deflecting elements 118, 120 are arranged at the same height with respect to the optical axis 151. The same is true of the other deflecting element 170. This measure advantageously makes it possible to minimise the overall height of an operating microscope fitted with the illuminating apparatus according to the invention. It is also possible to mount the deflecting elements 118, 120 in an offset position with respect to the optical axis 151, i.e. at different heights. Two deflecting elements thus offset from one another in the vertical direction may be acted upon by only one single light source using a corresponding beam splitter.

FIG. 3 shows part of the illuminating apparatus in greater detail. An optical system 102a is shown connected downstream of the light source 102. The illumination beam path 105 emanating from the optical system 102a strikes a Köster's prism 104 and is thereby split into the two illumination beam paths 106, 108, which, as described previously, first of all strike the first deflecting element 118 which supplies or illuminates only one observation beam path 152 of the main surgeon and only one observation beam path 156 of the assisting surgeon.

FIG. 4 shows another preferred embodiment of the illuminating apparatus according to the invention in a view corresponding to FIG. 2. Identical or similar components have been given the same reference numerals here. The following description will only discuss the differences between the embodiments according to FIG. 2 and FIG. 4.

The deflecting elements 118, 120 according to FIG. 4 are constructed as polarising splitters by means of which any incident light is broken down into its linearly polarised components. By way of example let us assume that the first deflecting element 118 reflects the part oscillating perpendicularly to the plane of the drawing in the direction of the object 200, and transmits the part oscillating parallel to the plane of the drawing.

The directions of polarisation together with the respective directions of propagation are indicated in FIG. 4 with the symbols "∥" for polarisation parallel to the plane of the drawing, "⊥" for polarisation perpendicular to the plane of the drawing, and "→" for the direction of propagation.

Accordingly, the deflecting element 120 is constructed so that the part of the light oscillating parallel to the plane of the drawing is reflected and the part oscillating perpendicularly to the plane of the drawing is transmitted.

Moreover, a λ/4 plate 400 is provided between the main objective lens 150 and the object 200. En route from the respective deflecting elements 118, 120 through the main objective lens 150 to the object 200 and back again, the λ/4 plate, in effect, acts as a λ/2 plate which rotates the plane of oscillation through 90°. Thus, as it travels from the object 200 back to the deflecting elements, light polarised parallel to the plane of the drawing strikes the deflecting element 118, and perpendicularly polarised light strikes the deflecting element 120. This is transmitted by the respective deflecting elements 118, 120 without being reflected. In particular, this ensures that light emanating from the object is not reflected back off the deflecting element 120 onto the deflecting element 118, and as a result crosstalk effects can be eliminated completely.

In addition to the λ/4 plate 400, a λ/2 plate (not shown) may be provided between the deflecting elements 118 and 120. This λ/2 plate causes a 90 degree rotation of the polarisation of the light transmitted by the deflecting element 118, so that light polarised perpendicularly to the plane of the drawing arrives at the deflecting element 120. As a result it is possible to ensure that the light reflected onto the object 200 by the two deflecting elements 118, 120 is polarised in the same direction. In this way, reflexes at the main objective lens 150, for example, can be further reduced.

The deflecting elements 118, 120 may be provided in a cohesive or uniform glass block (not shown). This makes it possible to reduce the number of glass/air surfaces, thus further reducing unwanted reflections. In the event of the deflecting elements 118, 120 being constructed with polarising properties, the λ/2 plate (not shown) could also be integrated in a glass block of this kind

What is claimed is:

1. An illuminating apparatus for an operating microscope, the microscope having two observation beam paths for a first observer and another two observation beam paths for a second observer, the illuminating apparatus comprising:
an illumination system configured to emanate light; and
a deflecting device arranged to deflect light emanating from the illumination system onto an object that is to be observed, wherein the deflecting device includes a first deflecting element associated with a first observation beam path for the first observer and a first observation beam path for the second observer, and a second deflecting element associated with a second observation beam path for the first observer and a second observation beam path for the second observer.

2. The illuminating apparatus according to claim 1, wherein the illumination system has only a single light source.

3. Illuminating apparatus according to claim 1, wherein the first and second deflecting elements illuminate the object at a first illumination angle with respect to the observation beam paths.

4. The illuminating apparatus according to claim 3, wherein the first illumination angle is in a range from 0° through 2°.

5. The illuminating apparatus according to claim 4, further comprising a further deflecting element for providing further illumination of the object at a larger illumination angle with respect to the observation beam paths than the first illumination angle.

6. The illuminating apparatus according to claim 5, wherein the larger illumination angle is approximately 6°.

7. The illuminating apparatus according to claim 1, wherein the first deflecting element and the second deflecting element are at the same spacing from a main objective lens of the microscope.

8. The illuminating apparatus according to claim 5, wherein the further deflecting element is arranged at the same height as the first and second deflecting elements.

9. The illuminating apparatus according to claim 1, wherein each of the first and second deflecting elements is a semitransparent mirror element.

10. The illuminating apparatus according to claim 5, wherein the further deflecting element is a semitransparent mirror element.

11. The illuminating apparatus according to claim 5, wherein the further deflecting element is a fully reflective mirror element.

12. The illuminating apparatus according to claim 5, wherein the further deflecting element includes at least one semitransparent minor portion and at least one fully reflective minor portion.

13. The illuminating apparatus according to claim 10, wherein the semitransparent minor element is associated with a further observation channel of the microscope for a documentation device.

14. The illuminating apparatus according to claim 1, wherein at least one of the first deflecting element and the second deflecting element includes at least one semitransparent mirror portion and at least one fully reflective minor portion.

15. The illuminating apparatus according to claim 1, further comprising a device for preventing unwanted reflexes and/or reflections within the operating microscope.

16. The illuminating apparatus according to claim 15, wherein the first and second deflecting elements have polarising properties, and wherein a λ/4 device is provided in the observation beam paths for the first and second observers.

17. The illuminating apparatus according to claim 16, wherein a λ/4 plate or film is provided in the observation beam paths for the first and second observers between the object and the main objective lens.

18. The illuminating apparatus according to claim 16, wherein a λ/4 plate or film is provided in the observation beam paths for the first and second observers between the main objective lens and the deflecting elements.

19. The illuminating apparatus according to claim 15, wherein a λ/2 device is interposed between the two deflecting elements.

20. The illuminating apparatus according to claim 1, wherein the first and second deflecting elements are formed in a uniform glass block.

21. An illuminating apparatus for an operating microscope, the microscope having two observation beam paths for a first observer and another two observation beam paths for a second observer, the illuminating apparatus comprising:
an illumination system configured to provide two parallel illumination beams; and
a deflecting device, arranged to deflect the two parallel illumination beams onto an object that is to be observed, wherein the deflecting device includes a first deflecting element associated with a first observation beam path for the first observer and a first observation beam path for the second observer, and a second deflecting element associated with a second observation beam path for the first observer and a second observation beam path for the second observer, wherein a horizontal projection of the first deflecting element essentially overlaps the first observation beam path for the first observer and the first observation beam path for the second observer, and a horizontal projection of the second deflecting element essentially overlaps the second observation beam path for the first observer and the second observation beam path for the second observer.

22. A stereomicroscope for use in performing surgical operations, the stereomicroscope comprising:
two observation beam paths for a first observer;
another two observation beam paths for a second observer;
an illumination system configured to emanate light; and
a deflecting device arranged to deflect light emanating from the illumination system onto an object that is to be observed, wherein the deflecting device includes a first deflecting element associated with a first observation beam path for the first observer and a first observation beam path for the second observer, and a second deflecting element associated with a second observation beam path for the first observer and a second observation beam path for the second observer.

* * * * *